United States Patent [19]
Taniguchi et al.

[11] Patent Number: 5,908,615
[45] Date of Patent: Jun. 1, 1999

[54] FERULIC ACID ESTER ANTIOXIDANT/UV ABSORBENT

[75] Inventors: Hisaji Taniguchi, Wakayama-ken; Eisaku Nomura, Wakayama; Takuo Tsuno; Seikou Minami, both of Wakayama-ken, all of Japan

[73] Assignees: Tsuno Food Industrial Co., Ltd.; Wakayama Prefecture, both of Wakayama, Japan

[21] Appl. No.: 08/690,691

[22] Filed: Jul. 31, 1996

Related U.S. Application Data

[62] Division of application No. 08/436,687, May 8, 1995, Pat. No. 5,688,991.

[30] Foreign Application Priority Data

May 11, 1994 [JP] Japan ..................................... 6-097485

[51] Int. Cl.$^6$ ............................... A61K 7/44; A61K 7/00; C07C 69/76
[52] U.S. Cl. .............................. 424/60; 424/59; 424/400; 424/401
[58] Field of Search .......................... 424/59, 60; 560/55, 560/57

[56] References Cited

U.S. PATENT DOCUMENTS 5,552,135  9/1996  Cioca et al. ............................... 424/59

*Primary Examiner*—Shelley A. Dodson
*Attorney, Agent, or Firm*—Pennie & Edmonds LLP

[57] ABSTRACT

An antioxidant/UV absorbent useful in cosmetics is formed of an ester of ferulic acid with an alkanol having 1 to 12 carbon atoms.

8 Claims, No Drawings

FERULIC ACID ESTER ANTIOXIDANT/UV ABSORBENT

This is a division of application Ser. No. 08/436,687, filed May 8, 1995 now U.S. Pat. No. 5,688,991.

BACKGROUND OF THE INVENTION

1. Field of the Invention

The present invention relates to an antioxidant, useful in cosmetics, and novel ferulic acid derivatives.

2. Description of the Related Art

Ferulic acid is useful as raw material for medicines, agricultural chemicals, cosmetics, dyes, and foods. However it does not have sufficient antioxidant and ultraviolet (UV) absorbent properties. Further, ferulic acid turns yellow when dissolved in an alkaline solution, and degrades when allowed to stand in air for a long period of time. In addition, the trans form of ferulic acid is solid at room temperature, and is usually handled as powder, which is difficult to handle in, for example, processing.

Meanwhile, 2-ethylhexyl p-methoxycinnamate, commercially available under a trade mark of PARSOL MCX, is used as a UV absorbent in cosmetics. However, it is thermally unstable, and does not exhibit sufficient antioxidant property.

SUMMARY OF THE INVENTION

It is, therefore, an object of the present invention to provide a ferulic acid derivative which has superior antioxidant/UV absorbent properties, is easy to handle and thermally stable.

In an aspect of the present invention, there is provided an antioxidant/UV absorbent comprising, as an effective or active component, at least one ferulic acid ester represented by the following formula (I):

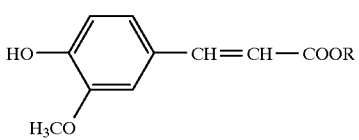
(I)

where R is an alkyl group having 1 to 12 carbon atoms.

Of the ferulic acid esters represented by formula (I), those in which R is an alkyl group has 4 to 12 carbon atoms are novel and are within the scope of the present invention.

In another aspect of the present invention, there is provided a cosmetic comprising a cosmetic base material, and an antioxidant and/or UV absorbent comprising at least one ferulic acid ester of formula (I).

DETAILED DESCRIPTION OF THE PREFERRED EMBODIMENT

The present inventors have made studies on antioxidant/UV absorbents easy to handle, thermally stable, which can be suitably used in cosmetics and found that certain esters of ferulic acid with certain alkanols exhibit such desirable properties. Such esters are represented by the formula (I):

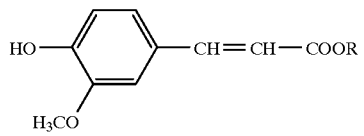
(I)

where R is an alkyl group having 1 to 12 carbon atoms.

Specific examples of R include methyl, ethyl, a $C_3$-alkyl group such as n-propyl, a $C_4$-alkyl group such as n-butyl, iso-butyl and tert-butyl), a $C_5$-alkyl group such as pentyl and iso-amyl, a $C_6$-alkyl group such as hexyl and cyclohexyl, a $C_7$-alkyl such as heptyl, a $C_8$-alkyl group such as octyl and 2-ethylhexyl, a $C_9$-alkyl group such as nonyl, a $C_{10}$-alkyl such as decyl, a $C_{11}$-alkyl such as undecyl, and a $C_{12}$-alkyl group such as dodecyl. The most preferred alkyl group is 2-ethylhexyl.

The ferulic acid esters represented by the formula (I) can be readily liquefied, or are liquid at room temperature, and thus can be easily handled. More specifically, the esters of formula (I) in which R is an alkyl group having 1 to 3 carbon atoms except for n-propyl is solid at room temperature, but becomes liquid by heating to 100° C. or less, preferably 80° C. or less except for isopropyl ester. The esters of formula (I) in which R is an alkyl group having 4 to 12 carbon atoms are liquid at room temperature. Therefore, the ferulic acid esters of formula (I) are easy to handle.

The ferulic acid esters of formula (I) are soluble in almost all organic solvents, also soluble in oils, but insoluble in water.

The ferulic acid esters of formula (I) can be prepared by reaction of ferulic acid with an alkanol, R—OH, where R is as defined above. Usually, ferulic acid and the alkanol are reacted in substantially equimolar amount.

Ferulic acid is known per se, and can be prepared by various methods. However, when the ferulic acid esters are used in cosmetics, it is preferred that ferulic acid be of natural origin. Thus, it is preferred to use a method disclosed in Japanese Patent Application Disclosure (Kokai) No. 5-331101 (corresponding to U.S. Pat. No. 5,288,902, which is hereby incorporated by reference).

Specific examples of the alkanol include methanol, ethanol, 1-propanol, 1-butanol, isobutyl alcohol, tert-butyl alcohol, 1-pentanol, isoamyl alcohol, 1-hexanol, cyclohexanol, 1-heptanol, 1-octanol, 2-ethylhexyl alcohol, 1-nonanol, 1-decanol, 1-undecanol, and 1-dodecanol. The most preferred alkanol is 2-ethylhexyl alcohol.

The reaction of ferulic acid with the alkanol is usually carried out in an organic solvent and in the presence of an acid catalyst. Sulfuric acid, hydrochloric acid, an organic sulfonic acid such as paratoluenesulfonic acid, or a cation exchange resin can be preferably used as the acid catalyst. The acid catalyst may be used in an amount of 1/15 to 1/350 moles per mole of ferulic acid. It is preferable to use the acid catalyst in a less amount within this range in view of cost.

The organic solvent preferably includes an aromatic solvent such as toluene, xylene, chlorobenzene, or benzene. The amount of the solvent is not particularly limited, but the solvent is usually used in an amount of 5 to 20 times, preferably 10 times the volume of 1 gram of ferulic acid.

The esterification reaction is usually conducted at 70 to 130° C., preferably at the boiling point of an organic solvent used (for example, 80° C. for benzene, and 110° C. for toluene). The esterification reaction is preferably carried out until almost no ferulic acid is detected, and is usually conducted for 6 to 15 hours.

The ferulic acid esters of formula (I) are preferably used as a component in cosmetics such as sun oil, sun care cream, sun screen lotion, hair spray, liquid foundation, anti-wrinkle essence, au de colon, and after-shaving lotion. The cosmetic of the present invention usually contains a cosmetic base material, and at least one ferulic acid ester of formula (I) in an amount of 1 to 15% by weight based on the total weight of the cosmetic composition.

The present invention will be more fully described with reference to the following Examples.

EXAMPLE 1

In a three-necked flask, 19.5 g (0.1 mole) of ferulic acid, 13.0 g (0.1 mole) of 2-ethylhexanol, and 200 ml of toluene as a solvent were placed, and 1.0 g of paratoluenesulfonic acid as an acid catalyst was added. This reaction mixture was stirred at 80° C. for 13 hours. After cooled, the mixture was washed with saturated aqueous solution of sodium hydrogen carbonate. The organic layer was dried over anhydrous magnesium sulfate, and decolored by activated carbon. The solvent toluene was fully evaporated off from the organic layer under reduced pressure to obtain 25.5 g (yield: 85%) of 2-ethylhexyl ferulate.
Properties: Viscous colorless liquid (at 25° C.)
IR spectra: 2960 cm$^{-1}$ (CH$_3$); 2861 cm$^{-1}$ (CH$_2$); 1700 cm$^{-1}$ (ester C=O); 1269, 1160 cm$^{-1}$ (ester C—O)
$^1$H NMR (DMSO-d$_6$): 0.45–15 ppm (15H, m, alkyl); 3.60 ppm (3H, s, O—CH3); 3.82 ppm (2H., d, —O—CH$_2$—); 6.08–7.50 ppm (5H, m, aromatic, and CH=CH); 9.30 ppm (1H, bs, OH). $^{13}$C NMR (CDCl$_3$): 11.051; 14.058; 22.997; 23.890; 29.010; 30.527; 38.951; 55.962; 66.905; 109.459; 114.795; 115.716; 123.030; 127.066; 144.645; 146.867; 148.004; 167.561 ppm. UV spectra (95% ethanol): $\lambda_{max}$ 327 nm ($\epsilon_{max}$ 19800)
Elemental Analysis: C$_{18}$H$_{26}$O$_4$ Found: C; 70.61%, H; 8.31% Calculated: C; 70.56%, H; 8.55%

EXAMPLE 2

The same procedure was followed as in Example 1, except that 1.0 g of sulfuric acid was used as an acid catalyst, and xylene was used as a solvent. Thus, 22 g (yield: 72%) of 2-ethylhexyl ferulate was obtained.

EXAMPLE 3

The same procedure was followed as in Example 1, except that chlorobenzene was used as a solvent. Thus, 21 g (yield: 69%) of 2-ethylhexyl ferulate was obtained.

EXAMPLE 4

The same procedure was followed as in Example 1, except that benzene was used as a solvent. Thus, 15 g (yield: 50%) of 2-ethylhexyl ferulate was obtained.

EXAMPLE 5

The same procedure was followed as in Example 1, except that dry hydrogen chloride was used as an acid catalyst. Thus, 12 g (yield: 39%) of 2-ethylhexyl ferulate was obtained.

EXAMPLE 6

The same procedure was followed as in Example 1, except that an ion exchange resin having a sulfonic acid group introduced therein (commercially available under a trade mark of DIAION SK1B) was used as an acid catalyst Thus, 18 g (yield: 59%) of 2-ethylhexyl ferulate was obtained.

EXAMPLE 7

In a three-necked flask, 19.4 g (0.1 mole) of ferulic acid, 6.01 g (0.1 mole) of n-propyl alcohol, and 1.0 g of paratoluenesulfonic acid were placed, and 200 ml of benzene was added. This reaction mixture was stirred at 78° C. for 15 hours. Thereafter, the same procedures were taken as in Example 1 to obtain 15.2 g (yield: 64%) of n-propyl ferulate.
Properties: Viscous colorless liquid (at room temperature)
IR spectra: 2960 cm$^{-1}$ (CH$_3$); 1726 cm$^{-1}$ (ester C=O)
$^1$H NMR (CDCl$_3$): 0.972 ppm (3H, t, CH$_3$; 1.666 ppm (2H, m, CH$_2$); 3.898 ppm (3H, s, O—CH$_3$); 4.136 ppm (2H, t, CH$_2$); 5.92 ppm (1H, s, OH); 6.255–7.61 (5H, m, aromatic and CH=CH).
Elemental Analysis: C$_{13}$H$_{16}$O$_4$ Found: C; 66.15%, H; 6.71% Calculated: C; 66.08%, H; 6.83%

EXAMPLE 8

The same procedures were followed as in Example 7, except that 18.6 g (0.1 mole) of dodecyl alcohol was used as an alkanol), obtaining 26 g (yield: 72%) of dodecyl ferulate.
Properties: Viscous colorless liquid (at 100° C.)
IR spectra: 2923 cm$^{-1}$ (CH$_2$); 1704 cm$^{-1}$ (ester C=O)
UV spectra (95% ethanol): $\lambda_{max}$ 327 nm ($\epsilon_{max}$ 21000)
$^1$H NMR (CDCl$_3$): 0.89 ppm (t, 3H, CH3); 1.29 ppm (bs, 20H, (CH$_2$)$_{10}$); 3.91 ppm (s, 3H, OCH$_3$); 4.21 ppm (t, 2H, CH$_2$); 6.20–7.83 ppm (m, 6H, aromatic, and CH=CH, OH);.
Elemental Analysis: C$_{22}$H$_{34}$O$_4$ Found: C; 72.63%, H; 9.57% Calculated: C; 72.89%, H; 9.45%

EXAMPLE 9

Use of 2-ethylhexyl ferulate as a component in sun oil

| Formulation | wt/wt (%) |
| --- | --- |
| 1. 2-ethylhexyl ferulate | 2.0–10.0 |
| 2. Liquid paraffin to make a total of | 100.0 |
| 3. Isopropyl myristate | 10.0 |
| 4. Coconut oil | 5.0 |
| 5. Natural vitamin E | 0.02 |
| 6. Perfume | 0.10 |

The components 1–6 were sequentially added at room temperature, and stirred well to dissolve them.

When the sun oil thus obtained was applied to the skin, it could impart sunburnt skin without causing erythema.

EXAMPLE 10

Use of 2-ethylhexyl ferulate as a component in sun care cream

| Formulation | wt/wt (%) |
| --- | --- |
| 1. Purified water | 54.08 |
| 2. 1,3-butylene glycol | 7.0 |
| 3. Methyl p-hydroxybenzoate | 0.3 |
| 4. Triethanolamine | 1.0 |
| 5. Titanium dioxide | 3.0 |
| 6. 2-ethyl hexyl ferulate | 10.0 |
| 7. Liquid paraffin | 10.0 |
| 8. Vaseline | 5.0 |
| 9. Cetanol | 3.0 |
| 10. Stearic acid | 3.0 |
| 11. Lipophilic glycerin monostearate | 3.0 |
| 12. Dimethylpolysiloxane | 0.5 |

-continued

| Formulation | wt/wt (%) |
| --- | --- |
| 13. Natural vitamin E | 0.02 |
| 14. Perfume | 0.1 |

The aqueous phase formed of the components 1–5 and the oily phase formed of the components 6–13 were each heated to 80° C. to dissolve the respective components. After the component 5 was fully dispersed in the aqueous phase, the oily phase was added to the aqueous phase. The mixture was stirred at a high speed to emulsify the components. The emulsion was cooled and the component 14 was added to obtain a uniform cream.

The sun care cream thus obtained fully functioned as a sun care cream.

EXAMPLE 11

Use of 2-ethylhexyl ferulate as a component in sun screen lotion

| Formulation | wt/wt (%) |
| --- | --- |
| 1. Purified water | 70.78 |
| 2. 1,3-butylene glycol | 7.0 |
| 3. Methyl parahydroxybenzoate | 0.3 |
| 4. Hydroxyethylcellulose | 0.3 |
| 5. 2-ethylhexyl ferulate | 10.0 |
| 6. Sorbitan monooleate | 1.0 |
| 7. POE(10) oleyl ether | 1.0 |
| 8. Isopropylmyristate | 5.0 |
| 9. Vaseline | 3.0 |
| 10. Cetanol | 1.0 |
| 11. Dimethylpolysiloxane | 0.5 |
| 12. Natural vitamin E | 0.02 |
| 13. Perfume | 0.1 |

The aqueous phase formed of the components 1–4 and the oily phase formed of the components 5–12 were each heated to 80° C. to dissolve the respective components. After the component 4 was fully swelled and dissolved in the aqueous phase, the oily phase was added to the aqueous phase. The mixture was stirred at a high speed to emulsify the components. The emulsion was cooled and the component 13 was added to obtain a uniform cream.

The sun screen lotion thus obtained fully functioned as a sun screen lotion.

EXAMPLE 12

Use of 2-ethylhexyl ferulate as a component in hair spray

| Formulation | wt/wt (%) |
| --- | --- |
| 1. Alkanolamine solution of acrylic resin | 10.0 |
| 2. Oleyl alcohol | 0.1 |
| 3. Methylphenylpolysiloxane | 0.2 |
| 4. 2-ethylhexyl ferulate | 1.0 |
| 5. Ethanol | 88.5 |
| 6. Perfume | 0.2 |

To the component 5, the components 1–4 and 6 were sequentially added, and the mixture was fully stirred to dissolve the components. This mixture was charged in a suitable vessel together with dimethyl ether at a volume ratio of 50:50 to prepare a hair spray.

The hair spray fully functioned as a hair spray.

EXAMPLE 13

Use of 2-ethylhexyl ferulate as a component in liquid foundation

| Formulation | wt/wt (%) |
| --- | --- |
| 1. Purified water | 54.58 |
| 2. 1,3-butylene glycol | 10.0 |
| 3. Bentonite | 0.5 |
| 4. Sorbitan POE(10)monostearate | 1.0 |
| 5. Triethanolamine | 1.0 |
| 6. Methyl parahydroxybenzoate | 0.3 |
| 7. Talc | 3.1 |
| 8. Titanium dioxide | 5.1 |
| 9. Red iron oxide | 0.4 |
| 10. Yellow iron oxide | 1.4 |
| 11. Black iron oxide | 0.1 |
| 12. 2-ethylhexyl ferulate | 10.0 |
| 13. Stearic acid | 2.5 |
| 14. Lipophilic glycerin monostearate | 2.8 |
| 15. Liguid paraffin | 8.0 |
| 16. Natural vitamin E | 0.02 |
| 17. Perfume | 0.1 |

The component 3 was dispersed in the component 2, and the dispersion was added to the component 1. The mixture was stirred at 80° C. at a high speed, and the components 4–6 were added thereto. The resultant mixture was fully stirred to prepare an aqueous phase. On the other hand, the components 7–11 were fully mixed and pulverized, and this mixture was added to the aqueous phase. Then, the mixture was fully stirred at 80° C. To this mixture, the components 12–16 heated and dissolved at 80° C. were added, and the resultant mixture was stirred at a high speed, and cooled. Thereafter, the component 17 was added and stirred uniformly.

The liquid foundation thus prepared fully functioned as a liquid foundation.

EXAMPLE 14

Use of 2-ethylhexyl ferulate as a component in anti-wrinkle essence

| Formulation | wt/wt (%) |
| --- | --- |
| 1. Purified water | 65.18 |
| 2. 1,3-butylene glycol | 8.0 |
| 3. Methyl parahydroxybenzoate | 0.3 |
| 4. Triethanolamine | 1.0 |
| 5. 2-ethylhexyl ferulate | 10.0 |
| 6. POE(10) cetyl ether | 2.0 |
| 7. Lipophilic glycerin monostearate | 2.0 |
| 8. Stearic acid | 3.0 |
| 9. Cetanol | 1.0 |
| 10. Liquid paraffin | 5.0 |
| 11. Soft cholesteryl lanolin fatty acid eater | 2.0 |
| 12. Vitamin E acetate | 0.2 |
| 13. Natural vitamin E | 0.02 |
| 14. Placenta extract | 0.2 |
| 15. Perfume | 0.1 |

The aqueous phase formed of the components 1–4 and the oily phase formed of the components 6–13 were each heated to 80° C. to dissolve the respective components. Then, the oily phase was added to the aqueous phase. The mixture was stirred at a high speed to emulsify the components. The emulsion was cooled and the components 14 and 15 were added and uniformly mixed.

The anti-wrinkle essence thus obtained fully functioned as an anti-wrinkle essence.

EXAMPLE 15

Use of 2-ethylhexyl ferulate as a component in au de colon

| Formulation | wt/wt (%) |
|---|---|
| 1. Ethanol | 80.0 |
| 2. Perfume | 4.0 |
| 3. POE(40) cured castor oil | 1.0 |
| 4. 2-ethylhexyl ferulate | 1.0 |
| 5. Purified water | 14.0 |

The components 2–4 were added to and dissolved in the component 1. This mixture was added with the component 5, and sealed. The mixture was allowed to stand in dark, cold place for several days, and filtered.

The au de colon thus prepared fully functioned as an au de colon.

EXAMPLE 16

Use of 2-ethylhexyl ferulate as a component in after-shaving lotion

| Formulation | wt/wt (%) |
|---|---|
| 1. Ethanol | 55.0 |
| 2. Dipropylene glycol | 3.0 |
| 3. POE(40) cured castor oil | 2.0 |
| 4. 2-ethylhexyl ferulate | 1.0 |
| 5. Perfume | 0.1 |
| 6. L-menthol | 0.05 |
| 7. Purified water | 38.75 |
| 8. Dipotassium | 0.1 |

The components 2–6 were sequentially added to the component 1, and stirred and dissolved therein. The resultant mixture was added with a solution of the component 8 in the component 7, and fully stirred.

The after-shaving lotion thus prepared fully functioned as an after-shaving lotion.

EXAMPLE 17

According to the stability test (AOM test) against autoxidation in standard fats and oils analysis method, the stability test was conducted. Specifically, 1000 ppm of each compound listed in Table 1 below was added to purified lard oil to prepare samples. After 3 and 7 hours each, peroxide value (POV) was measured for each sample. The results are shown also in Table 1.

TABLE 1

| | POV | |
|---|---|---|
| Compound | After 3 hours | After 7 hours |
| 2-ethylhexyl ferulate | 14.1 | 50.3 |
| 2-ethylhexyl p-methoxy-cinnamate | 181.5 | 422.1 |
| None (blank) | 188.1 | 452.8 |

As can be seen from Table 1, the sample added with 2-ethylhexyl ferulate of the invention exhibited markedly improved antioxidation property over the other samples.

EXAMPLE 18

A thermal stability test was conducted on the compounds listed in Table 2 below. The results are shown also in Table 2.

TABLE 2

| Compound | Decomposition point (°C.) |
|---|---|
| Ferulic acid | 176.3 |
| 2-ethylhexyl ferulate | 196.9 |
| 2-ethylhexyl p-methoxy-cinnamate | 169.0 |

As can be seen from Table 2, 2-ethylhexyl ferulate has an improved thermal stability over ferulic acid and 2-ethylhexyl p-methoxycinnamate.

What is claimed is:

1. A cosmetic containing a base material, and an antioxidant/UV absorbent comprising at least one ferulic acid ester represented by formula (I):

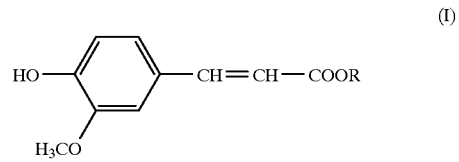

where R is an alkyl group having 4 to 12 carbon atoms.

2. The cosmetic according to claim 1, wherein said ferulic acid ester is 2-ethylhexyl ferulate.

3. A method for reducing the amount of ultraviolet light reaching a human body comprising applying to the body an effective amount of at least one ferulic acid ester of formula (I):

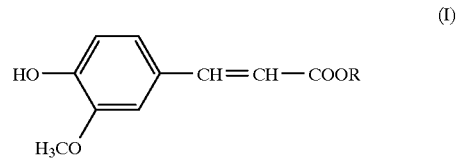

wherein R is an alkyl group having 1 to 12 carbon atoms.

4. The method of claim 3 wherein R is an alkyl group having 4 to 12 carbon atoms.

5. The method of claim 3 wherein said ferulic acid ester of formula (I) is 2-ethylhexyl ferulate.

6. A method for inhibiting oxidation of a cosmetic comprising adding to the cosmetic an effective amount of at least one ferulic acid ester of formula (I):

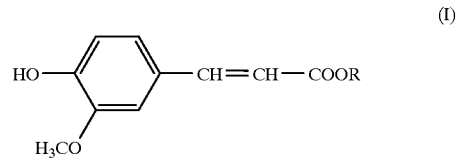

wherein R is an alkyl group having 1 to 12 carbon atoms.

7. The method of claim 6 wherein R is an alkyl group having 4 to 12 carbon atoms.

8. The method of claim 6 wherein said ferulic acid ester of formula (I) is 2-ethyhexyl ferulate.

* * * * *